(12) United States Patent
Meister et al.

(10) Patent No.: US 11,184,719 B2
(45) Date of Patent: Nov. 23, 2021

(54) MULTICHANNEL OPTO-MECHANICAL STIMULATION

(71) Applicant: MED-EL Elektromedizinische Geraete GmbH, Innsbruck (AT)

(72) Inventors: Dirk Meister, Innsbruck (AT); Darshan Shah, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 513 days.

(21) Appl. No.: 15/750,223

(22) PCT Filed: Aug. 10, 2016

(86) PCT No.: PCT/US2016/046257
§ 371 (c)(1),
(2) Date: Feb. 5, 2018

(87) PCT Pub. No.: WO2017/027542
PCT Pub. Date: Feb. 16, 2017

(65) Prior Publication Data
US 2018/0234778 A1    Aug. 16, 2018

Related U.S. Application Data

(60) Provisional application No. 62/203,507, filed on Aug. 11, 2015.

(51) Int. Cl.
*H04R 25/00* (2006.01)
*A61N 1/36* (2006.01)
(Continued)

(52) U.S. Cl.
CPC ............. *H04R 25/606* (2013.01); *A61F 2/18* (2013.01); *A61N 1/36039* (2017.08);
(Continued)

(58) Field of Classification Search
CPC ........ H04R 25/606; H04R 25/353–356; H04R 25/50–507; H04R 2225/41; H04R 2225/43; A61N 1/36038
See application file for complete search history.

(56) References Cited

U.S. PATENT DOCUMENTS

| 4,223,180 A | 9/1980 | Eckels |
| 5,983,139 A | 11/1999 | Zierhofer |
| 2016/0022991 A1* | 1/2016 | Apoux ................. A61N 1/0541 607/57 |

FOREIGN PATENT DOCUMENTS

WO    2014/164814    10/2014

OTHER PUBLICATIONS

Dietz et al., "Emphasis of Spatial Cues in the Temporal Fine Structure During the Rising Segments of Amplitude-Modulated Sounds," PNAS, vol. 110, No. 37, Sep. 10, 2013, p. 15151-15156 (Year: 2013).*

(Continued)

*Primary Examiner* — Thaddeus B Cox
(74) *Attorney, Agent, or Firm* — Sunstein LLP

(57) ABSTRACT

A signal processing arrangement generates optical stimulation signals to optical stimulation contacts in an implanted cochlear implant array. An input sound signal is transformed into band pass signals that each represent an associated band of audio frequencies, with each band pass signal includes an envelope component characterizing loudness of the band pass signal, and a fine structure component characterizing temporal details of the band pass signal. One or more of the signal components of each band pass signal is half wave rectified to remove negative phase signals. Signal slope is determined that corresponds to rate of change of the rectified one or more signal components. Then constant-rate optical stimulation pulses are generated for one or more given band signals only when the rectified one or more signal components has a positive signal slope.

15 Claims, 7 Drawing Sheets

(51) Int. Cl.
G02C 11/06 (2006.01)
A61F 2/18 (2006.01)
(52) U.S. Cl.
CPC ........ *G02C 11/06* (2013.01); *A61F 2002/183* (2013.01); *H04R 2225/67* (2013.01)

(56) References Cited

OTHER PUBLICATIONS

International Search Report—International Application No. PCT/US16/46257, dated Oct. 25, 2016 together with the Written Opinion of the International Searching Authority, 15 pages.

Shamma al. "On the balance of envelope and temporal fine structure in the encoding of speech in the early auditory system," Journal of the Acoustical Society of America, vol. 133, No. 5, pp. 2818-2833, May 2013.

Hindawi Publishing Corporation "DSP in Hearing Aids and Cochlear Implants," EURASIP Journal on Applied Signal Processing, vol. 18, 2911-3086, Jan. 2005.

Fontaine et al. "Brian hears: online auditory processing using vectorization over channels," Frontiers in Neuroinformatics, vol. 5, Article 9, 9 pages, Jul. 22, 2011.

Izzo et al. "Laser Stimulation of Auditory Neurons: Effect of Shorter Pulse Duration and Penetration Depth," Biophysical Journal, vol. 94, No. 5, 3159-3166, Apr. 2008.

Zhang et al. "Optoacoustic induced vibrations within the inner ear," Optics Express, vol. 17, No. 25, 23037-23043, Dec. 7, 2009.

Zhang et al. "Effects of heat conduction on the spatial selectivity of infrared stimulation in the cochlea," BioMedical Engineering OnLine, vol. 14, No. 23, 12 pages, 2015.

\* cited by examiner

MULTICHANNEL OPTO-MECHANICAL STIMULATION

This application is a national phase entry of Patent Cooperation Treaty Application PCT/US2016/046257, filed Aug. 10, 2016, which in turn claims priority from U.S. Provisional Patent Application 62/203,507, filed Aug. 11, 2015, both of which are incorporated herein by reference in their entireties.

FIELD OF THE INVENTION

The present invention relates to hearing implant systems, and more specifically, to techniques for using opto-mechanical stimulation in such systems.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, this electrode array 110 includes multiple stimulation contacts 112 on its surface that provide selective stimulation of the cochlea 104. Depending on context, the stimulation contacts 112 are also referred to as electrode channels. In cochlear implants today, a relatively small number of electrode channels are each associated with relatively broad frequency bands, with each stimulation contact 112 addressing a group of neurons through an electric stimulation pulse having a charge which is derived from the instantaneous amplitude of the signal envelope within that frequency band.

FIG. 2 shows the major functional blocks in a typical cochlear implant signal processing system wherein band pass signals are processed and coding to generate electrical stimulation signals to stimulation electrodes in an implanted cochlear implant electrode array. For example, commercially available Digital Signal Processors (DSP) can be used to perform speech processing according to a 12-channel CIS approach. The initial acoustic audio signal input is produced by one or more sensing microphones, which may be omni-directional and/or directional. Preprocessor Filter Bank 201 pre-processes the initial acoustic audio signal with a bank of multiple band pass filters, each of which is associated with a specific band of audio frequencies—for example, a digital filter bank having 12 digital Butterworth band pass filters of 6th order, Infinite Impulse Response (IIR) type—so that the acoustic audio signal is filtered into some M band pass signals, $B_1$ to $B_M$ where each signal corresponds to the band of frequencies for one of the band pass filters. Each output of the CIS band pass filters can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 201 may be implemented based on use of a fast Fourier transform (FFT) or a short-time Fourier transform (STFT). Based on the tonotopic organization of the cochlea, each stimulation contact in the scala tympani often is associated with a specific band pass filter of the external filter bank.

FIG. 3 shows an example of a short time period of an audio speech signal from a microphone, and FIG. 4 shows an acoustic microphone signal decomposed by band-pass filtering by a bank of filters into a set of signals. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety:

```
for j = 0 to number of channels − 1 do
    for s = 0 to number of samples − 1 do
        Y_j(s) = B_{0j} *X_j(s) + Z_{0j}
        for i = 0 to order− 3 do
            Z_ij = B_{i+1, j} *X_j(s) + Z_{i+1,j} − A_{i+1, j} * Y_j(s)
        end for
        Z_{order−2,J} = B_{order− 1,j} * X_j(s) −A_{order−1,j} * Y_j(s)
    end for
end for
```

The band pass signals $B_1$ to $B_M$ (which can also be thought of as frequency channels) are input to a Signal Processor 202 which extracts signal specific stimulation information—e.g., envelope information, phase information, timing of requested stimulation events, etc.—into a set of N stimulation channel signals $S_1$ to $S_N$ that represent electrode specific requested stimulation events. For example, channel specific sampling sequences (CSSS) may be used as described in U.S. Pat. No. 6,594,525, which is incorporated herein by reference in its entirety. For example, the envelope extraction may be performed using 12 rectifiers and 12 digital Butterworth low pass filters of 2nd order, IIR-type.

A Pulse Generator 205 includes a Stimulation Coding Module 203 that codes the stimulation channel signals $S_1$ to $S_N$ to produce a set of coded electrical stimulation signals $A_1$ to $A_M$ that provide an optimal electric representation of the acoustic signal. The coded electrical stimulation signals $A_1$ to $A_M$ may be symmetrical biphasic current pulses with amplitudes that are directly obtained from the compressed envelope signals.

The Pulse Generator 205 also includes a Pulse Mapping and Shaping Module 204 that develops the coded electrical stimulation signals $A_1$ to $A_M$ into a set of output electrode pulses $E_1$ to $E_M$ for the stimulation contacts in the implanted electrode array which stimulate the adjacent nerve tissue. Specifically, the Pulse Mapping and Shaping Module 204 applies a non-linear mapping function (typically logarithmic) to the amplitude of each band-pass envelope. This mapping function—for example, using instantaneous non-linear compression of the envelope signal (map law)—typically is adapted to the needs of the individual cochlear implant user during fitting of the implant in order to achieve natural loudness growth. This may be in the specific form of functions that reflect patient-specific perceptual characteristics A logarithmic function with a form-factor C typically may be applied as a loudness mapping function, which typically is identical across all the band pass analysis channels. In different systems, different specific loudness mapping functions other than a logarithmic function may be used, with just one identical function is applied to all channels or one individual function for each channel In the specific case of a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

Another cochlear implant stimulation strategy that does transmit fine time structure information is the Fine Structure Processing (FSP) strategy by Med-El. Zero crossings of the band pass filtered time signals are tracked, and at each negative to positive zero crossing, a Channel Specific Sampling Sequence (CSSS) is started. Typically CSSS sequences are only applied on the first one or two most apical electrode channels, covering the frequency range up to 200 or 330 Hz.

The FSP arrangement is described further in Hochmair I, Nopp P, Jolly C, Schmidt M, Schößer H, Garnham C, Anderson I, MED-EL *Cochlear Implants: State of the Art and a Glimpse into the Future*, Trends in Amplification, vol. 10, 201-219, 2006, which is incorporated herein by reference.

Many cochlear implant coding strategies use what is referred to as an N-of-M approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

One method to reduce the spectral clustering of stimulation per time frame is the MP3000™ coding strategy by Cochlear Ltd, which uses a spectral masking model on the electrode channels. Another method that inherently enhances coding of speech onsets is the ClearVoice™ coding strategy used by Advanced Bionics Corp, which selects electrode channels having a high signal to noise ratio. U.S. Patent Publication 2005/0203589 (which is incorporated herein by reference in its entirety) describes how to organize electrode channels into two or more groups per time frame. The decision which electrode channels to select is based on the amplitude of the signal envelopes.

In addition to the specific processing and coding approaches discussed above, different specific pulse stimulation modes are possible to deliver the stimulation pulses with specific stimulation contacts—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc. But some stimulation arrangements are quite power consuming, especially when neighboring stimulation contacts are used as current sinks. Up to 10 dB more charge might be required than with simple mono-polar stimulation concepts (if the power-consuming pulse shapes or stimulation modes are used continuously).

One limit in using cochlear implants that deliver electrical stimulation to cochlear tissues is the effect of stimulation current dispersion in the tissues and the resulting limit on spatial selectivity. Instead of electrical stimulation, optical stimulation of cochlear tissues has been proposed using pulsed delivery of infrared light that causes local tissue heating leading to a sound percept. Limiting the pulse duration of the optical stimulation appears to avoid tissue damage, and it is believed that optical stimulation might offer better spatial selectivity characteristics than electrical stimulation. But the power requirements for such an arrangement are highly challenging and it has not yet been demonstrated that chronic optical stimulation is safe and effective. And existing electrical stimulation strategies are likely to require some modification to be usable for optical stimulation.

SUMMARY OF THE INVENTION

Embodiments of the present invention are directed to a signal processing arrangement and corresponding method that generates optical stimulation signals to optical stimulation contacts in an implanted cochlear implant array. An input sound signal is transformed into band pass signals that each represent an associated band of audio frequencies, with each band pass signal having an envelope component characterizing loudness of the band pass signal, and a fine structure component characterizing temporal details of the band pass signal. One or more of the signal components of each band pass signal is half wave rectified to remove negative phase signals. Signal slope is determined that corresponds to rate of change of the rectified one or more signal components. Then constant-rate optical stimulation pulses are generated for one or more given band signals only when the rectified one or more signal components has a positive signal slope. The optical stimulation pulses are amplitude modulated based on the corresponding envelope component to develop the optical stimulation signals for delivery by the optical stimulation contacts to adjacent auditory neural tissue.

In further specific embodiments, amplitude modulating the optical stimulation pulses may further be based on patient-specific stimulation characteristics. For a given band pass signal the fine structure component and/or the envelope component may be half wave rectified. And generating the plurality of constant-rate optical stimulation pulses may commence at positive slopes of the rectified one or more signal components.

DETAILED DESCRIPTION OF SPECIFIC EMBODIMENTS

It is known that if residual hearing is present, hearing sensation can be induced by optical stimulation using laser light to create mechanical displacement of cochlear tissue such as the cochlear fluid or the basilar membrane. If the laser light is delivered in short pulses with high pulse peak power, or over a sufficient amount of time at fixed energy, stress and thermal confinement can be overcome to produce a loud click sound.

Figure 5:
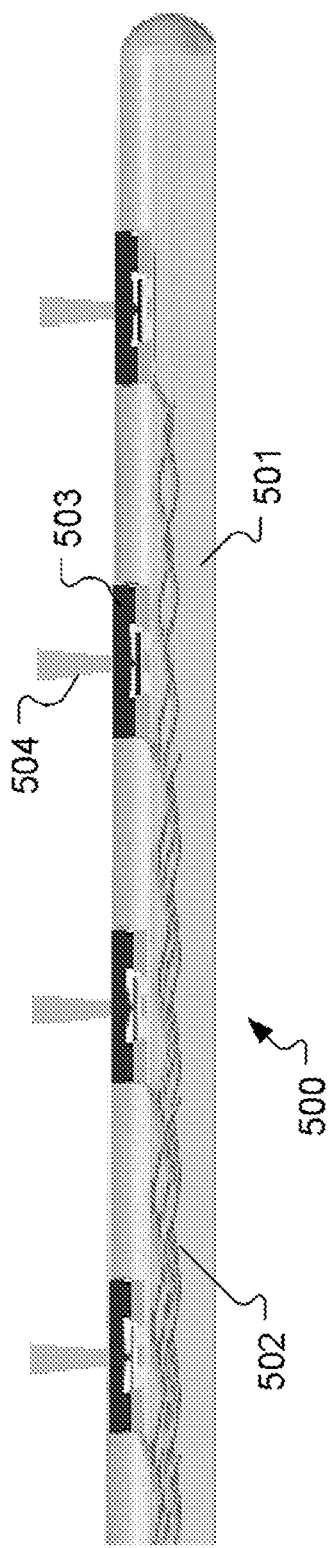
FIG. 5 shows a portion of a cochlear implant array with optical stimulation contacts according to an embodiment of the present invention.

FIG. 5 shows an example of a portion of cochlear implant array 500 that includes multiple laser led stimulation contacts 503 embedded in an electrode carrier 501 made of biocompatible resilient material and receiving optical stimulation signals via electrode lead wires 502 from an implanted stimulator (not shown). The laser led stimulation contacts 503 on the multi-channel cochlear implant array 500 can apply locally restricted, focused light pulses 504 on or near the basilar membrane of the cochlea and induce mechanical displacement in the basilar membrane. This optical stimulation may induce two different frequency responses: a tonotopic frequency response at the stimulation site on the basilar membrane, and another frequency response at the pulse repetition frequency. In addition, different wavelengths of light may contribute different energies based on absorption of water and haemoglobin in and around the cochlea.

Figure 6:
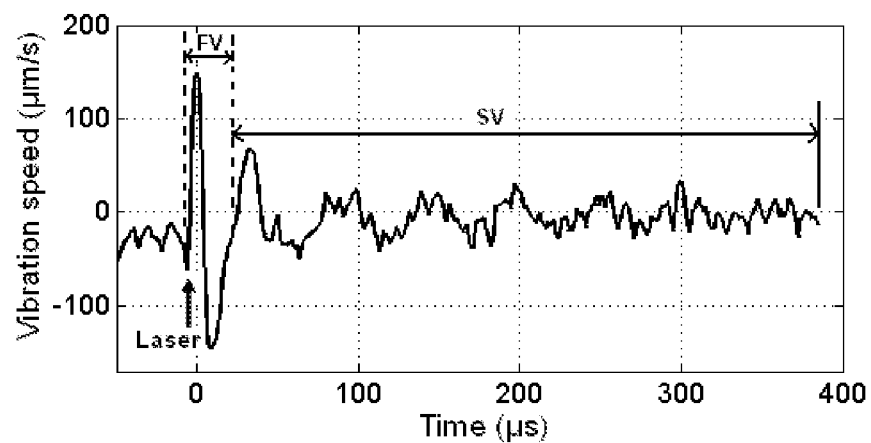
FIG. 6 shows a waveform depicting basilar membrane vibration following optical stimulation.

FIG. 6 shows a waveform depicting basilar membrane vibration following optical stimulation, taken from Zhang et al., *Optoacoustic induced vibrations within the inner ear*, Opt. Express 17, 23037-23043 (2009); which is incorporated herein by reference in its entirety. Directly after application of the laser pulse, the basilar membrane is pushed in one direction, shown by the initial sharp positive peak. The interval with that first positive peak and the following first negative peak is marked as FV and is referred to by Zhang as "fast vibration," and the following interval marked as SV is referred to as "slow vibration". The SV following the FV has a frequency corresponding to the resonant frequency represented in the respective optical stimulated cochlear segment. Signal processing for multi-channel optical stimulation includes conventional frequency analysis with a filter bank. Each laser diode along the implanted array is assigned to a filter band (frequency channel) according to the tonotopic location of the laser induced basilar membrane displacement, and the diodes within a given frequency channel are amplitude modulated according to the band pass signals.

Figure 1:
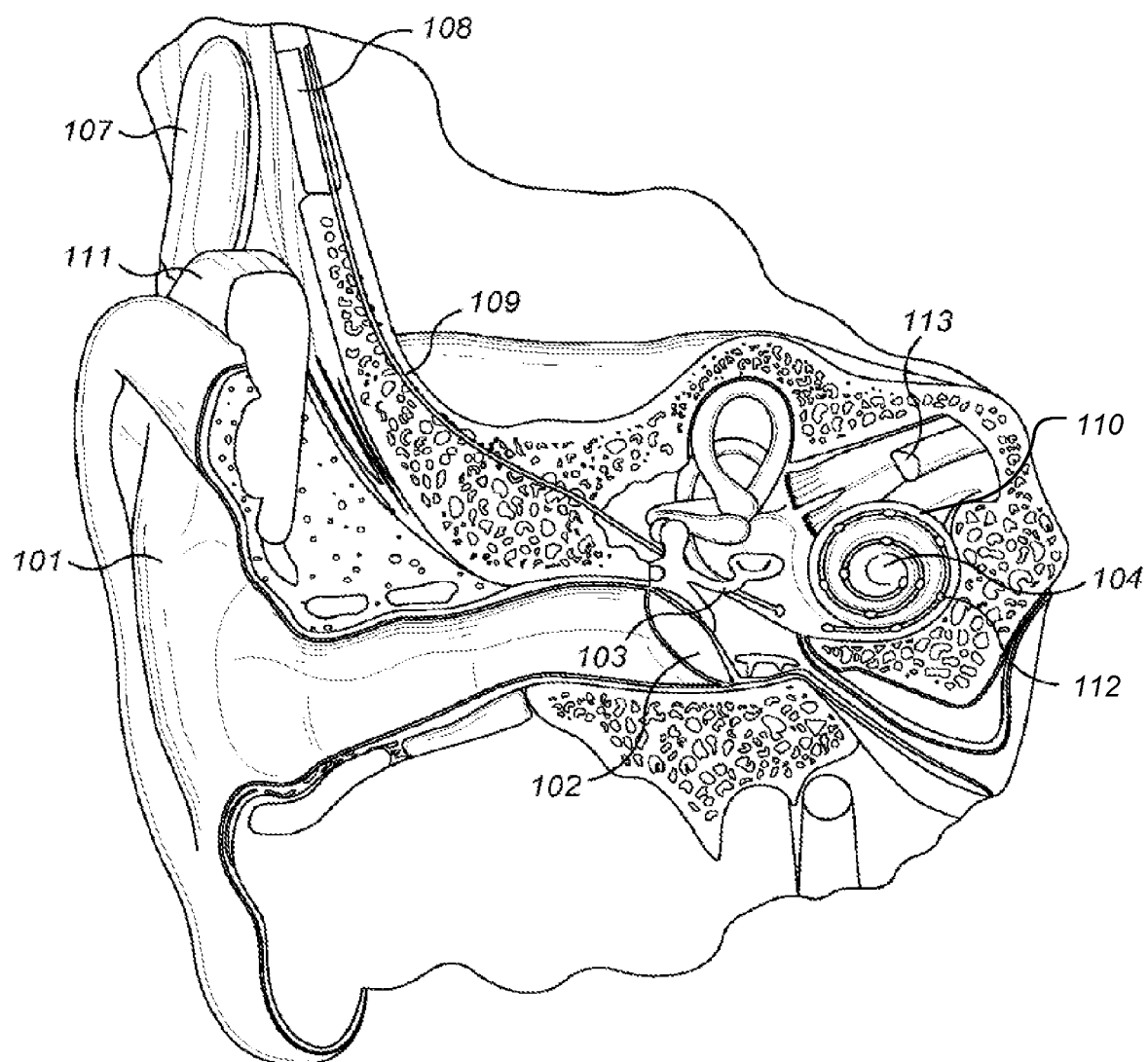
FIG. 1 shows a section view of a human ear with a typical auditory prosthesis system designed to deliver electric stimuli to the inner ear and acoustic stimuli at the ear canal.
Figure 2:
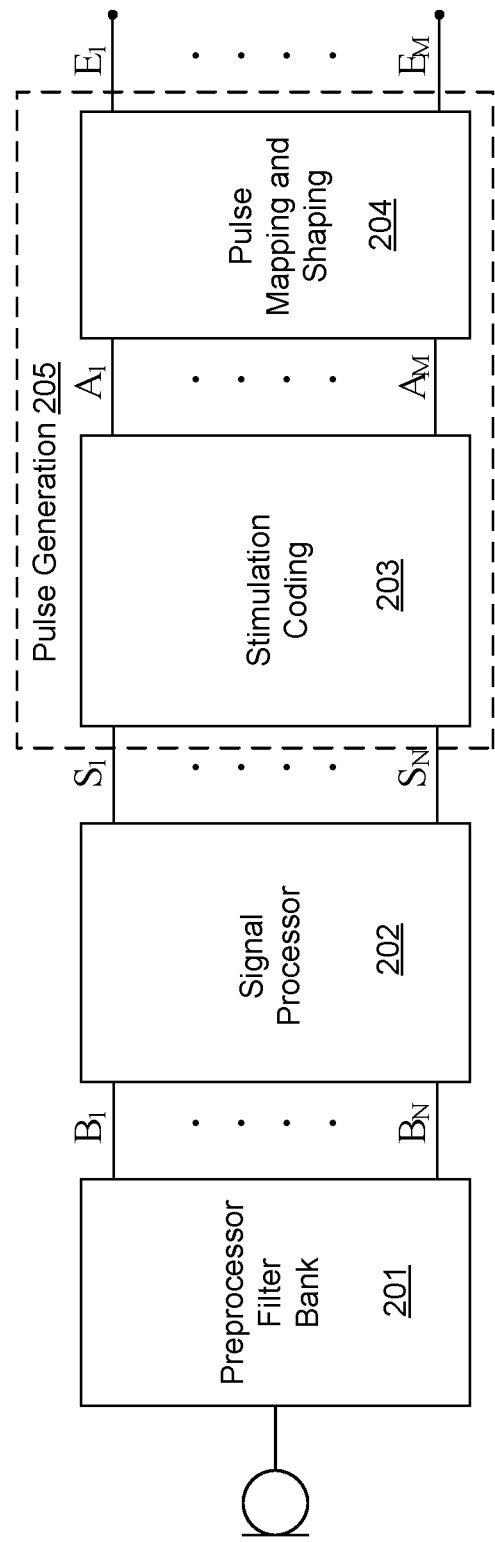
FIG. 2 shows various functional blocks in a continuous interleaved sampling (CIS) processing system.
Figure 3:
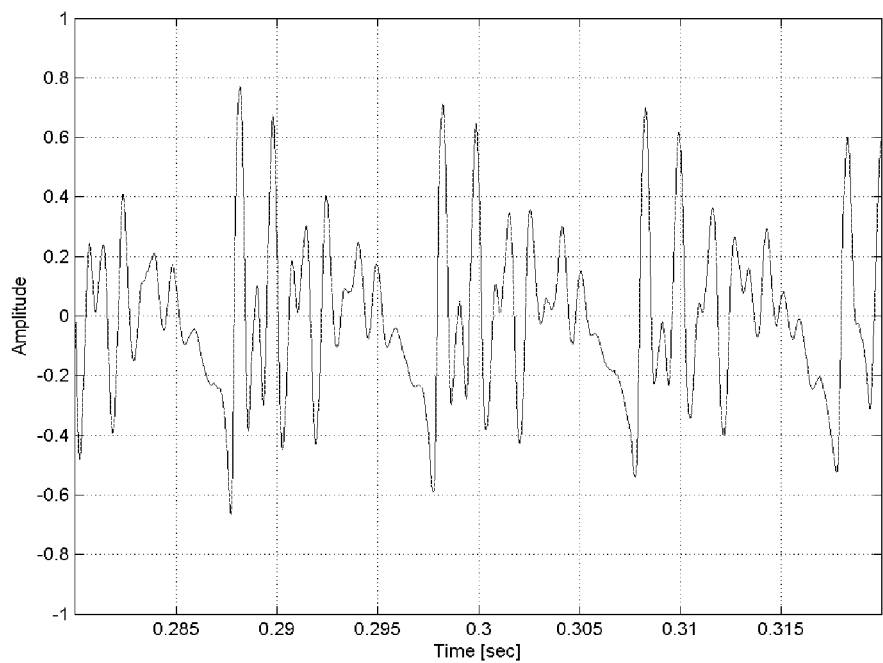
FIG. 3 shows an example of a short time period of an audio speech signal from a microphone.
Figure 4:
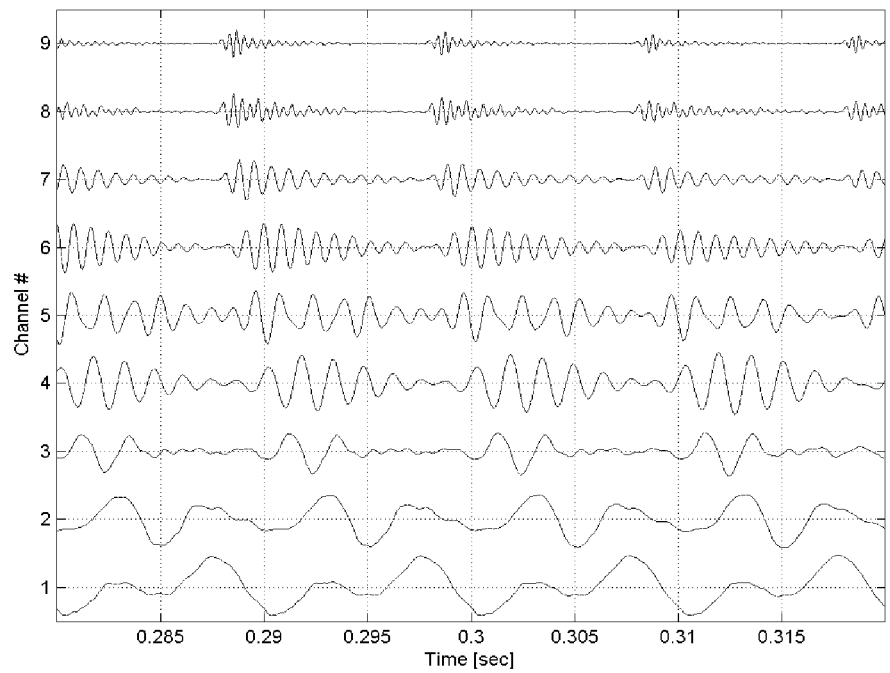
FIG. 4 shows an acoustic microphone signal decomposed by band-pass filtering by a bank of filters into a set of band pass signals.
Figure 7:
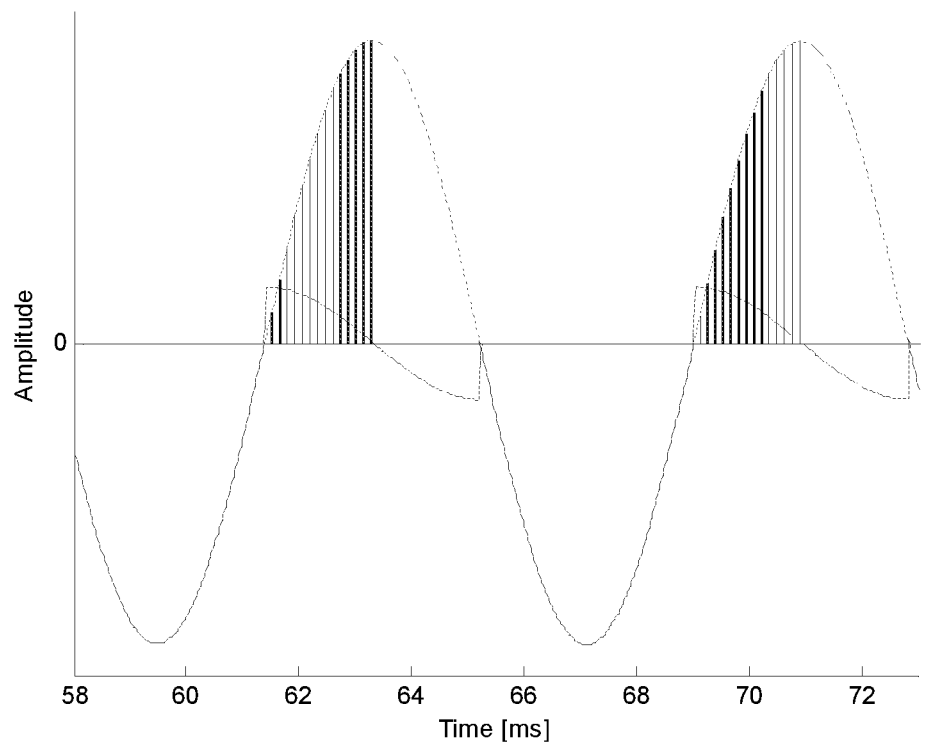
FIG. 7 shows an example of constant-rate optical stimulation pulses according to an embodiment of the present invention.
Figure 8:
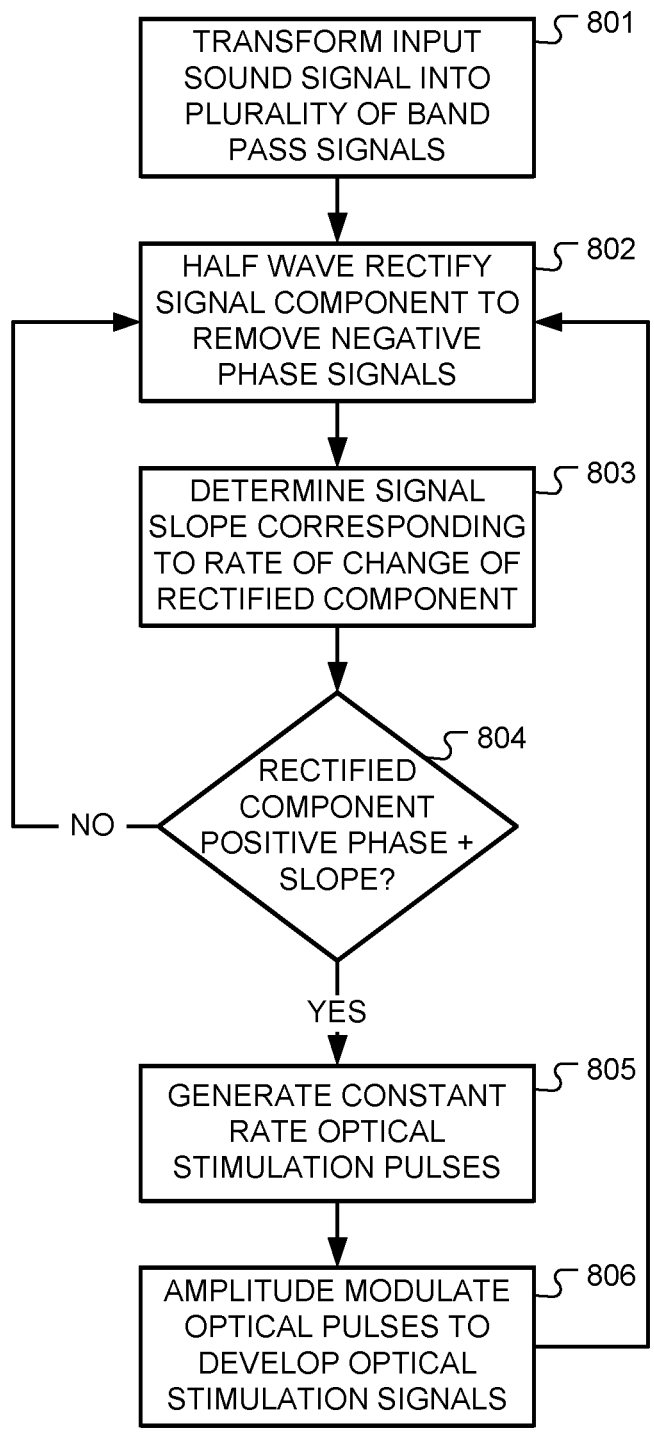
FIG. 8 is a flow chart showing various logical steps in producing optical stimulation signals according an embodiment of the present invention.

FIG. 7 shows an example of constant-rate optical stimulation pulses during the positive signal slope of the band pass signal defining a stimulation burst and FIG. 8 is a flow chart showing various logical steps in producing optical stimulation signals to optical stimulation contacts in an implanted cochlear implant array according to an embodiment of the present invention. As in the arrangement discussed above with respect to FIG. 2, a preprocessor signal filter bank 201 can be configured to transform an input sound signal into band pass signals $B_1$ to $B_M$, step 801, that each represent an associated frequency band of audio frequencies. Each band pass signal includes an envelope component that characterizes the loudness of the band pass signal, and a fine structure component that characterizes the temporal details of the band pass signal. In FIG. 7, the sine wave shown is a portion of the band pass signal for the syllable "bet" with frequency boundaries of 100 and 200 Hz. Further depicted in FIG. 7 is the derivative during the half-wave rectified periods of the band pass signal, starting with a positive phase indicating the positive signal slope of the band pass signal and having a zero crossing at the maximum band pass signal and thereafter the negative phase indicating the negative signal slope of the band pass signal. FIG. 7 also shows the resulting constant-rate optical stimulation pulses $S_1$ to $S_N$ as the sequences of vertical black bars that commence at a negative-to-positive zero crossing of the rectified one or more band pass signal components.

The signal processing module 202 processes the band pass signals $B_1$ to $B_M$ to produce an initial set of optical stimulation pulses $S_1$ to $S_N$. Initially, the signal processing module 202 half wave rectifies one or more of the signal components of each band pass signal $B_1$ to $B_M$—the fine structure component and/or the envelope component—step 802, to remove negative phase signals. For example, with respect to FIG. 7, the lower negative phase of the fine structure component of the band pass signal shown is removed, leaving the positive phases and only during their positive signal slope, the constant-rate optical stimulation pulses are applied.

The signal processing module 202 then determines the signal slope that corresponds to rate of change of the rectified one or more signal components, step 803. When the rectified one or more signal components has a positive signal slope, step 804, the signal processing module 202 generates constant-rate optical stimulation pulses $S_1$ to $S_N$, step 805, as in these periods the basilar membrane can be considered to be "pushed away" by the band pass signal. Otherwise signal processing module 202 stops or does not generate optical stimulation pulses. In terms of the basilar membrane vibration waveform depicted in FIG. 6, the elasticity of the membrane drives the membrane back towards its resting position within a few microseconds within the second phase of the FV fast vibration interval. Consequently, the signal processing module 202 can produce the optical stimulation pulses $S_1$ to $S_N$ during the positive signal slope portion of the rectified one or more signal components and stimulation pulses are skipped during the negative signal slope portions. To prevent oscillations of the basilar membrane with FV, the optical stimulation rate can be chosen to be different from the resonance frequency FV, e.g. slightly higher or lower. The optical stimulation pulses may have scaled amplitudes in this case, such that the desired amount of stimulation energy is still applied. For example the scaling may be linear mapping, with for example an adjustable constant parameter. In a further embodiment the scaling may be an exponentially decaying mapping function during the stimulation burst. This allows for controlling the deflection of the basilar membrane by the optical stimulation pulses.

The scaled amplitudes may be derived by applying puretone audiometry. For each optical stimulation contact a pure tone having a frequency of the respective resonance frequency at the stimulated cochlear segment is presented to the patient. Initially the scaling parameter is set to a value, such that with applying the mapping function no scaling happens. For example for a linear mapping function, where the stimulation pulse is derived from the fine structure signal, the scaling parameter is chosen in the way that the applied stimulation pulse equals the stimulation pulse without scaling, i.e. the mapping function becomes an identity mapping. The patient may change the scaling parameter in both directions, until he perceives the loudest pure tone. Scaling parameters deviating from this optimal setting may be perceived as blurry and/or muted.

Alternatively or in addition, for optimal transmission of optical stimulation energy, the stimulation burst repetition rate can be tuned to the frequency of SV or integer multiples of SV. Tuning to SV may for example be achieved by setting the frequency boundaries of the respective band pass filters properly. The signal processing module 202 may comprise a counter to control generation of stimulation burst repetition rate at integer multiples N of SV. In one embodiment the integer multiples for the band pass signals $B_1$ to $B_M$ may differ, i.e. N may be band pass specific. This may help to reduce the high stimulation burst rate and consequently lowers power consumption as well as heating of cochlear tissue due to power dissipation. In a further embodiment the integer multiples N may be less than the relaxation time of SV, for example less than 7 cycles.

The Stimulation Coding Module 203 then is configured to convert the optical stimulation pulses $S_1$ to $S_N$ to produce a corresponding sequence of optical stimulation signals $A_1$ to $A_M$, step 806, that provide an optimal electric representation of the acoustic signal, and the Pulse Mapping and Shaping Module 204 then applies a linear mapping function (typically logarithmic) and pulse shaping of the optical stimulation output signals $E_1$ to $E_M$ that is adapted to the needs of the individual implant user based on a post-surgical fitting process that determines patient-specific perceptual characteristics. Specifically, the optical stimulation pulses $S_1$ to $S_N$ may be amplitude modulated based on the corresponding envelope component to develop the optical stimulation output signals $E_1$ to $E_M$ for delivery by the optical stimulation contacts to adjacent auditory neural tissue.

Figure 9:
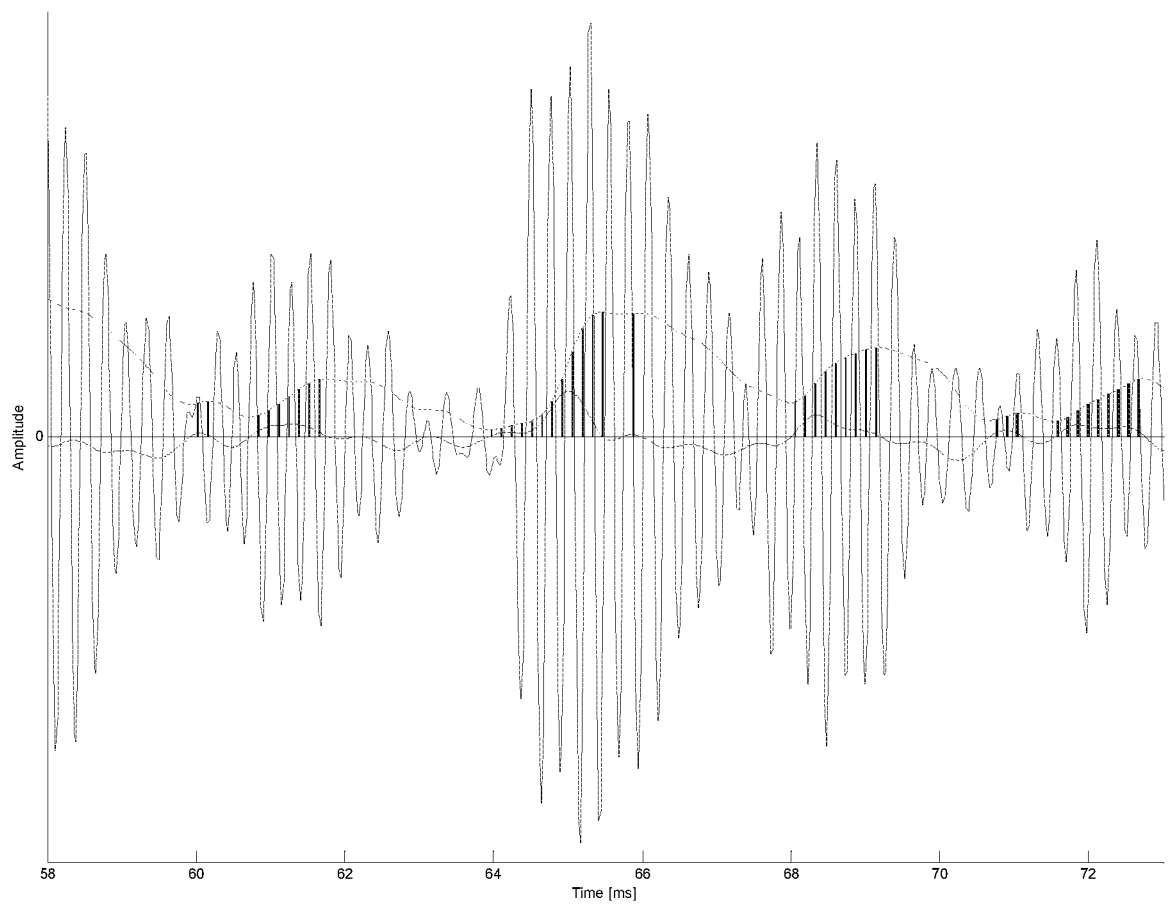
FIG. 9 shows another example of constant-rate optical stimulation pulses according to an embodiment of the present invention.

For higher frequency bands, the band pass frequency can be too high for the fine structure component to be directly used with the constant-rate pulse sequences. Above a certain upper limit of the band pass frequency, a low pass filter can be applied to the rectified band pass signal, to extract the envelope component, which then can be used for coding of the optical stimulation pulses. The upper frequency limit can be determined based on the relation of the optical stimulation pulse rate to the upper frequency boundary of the corresponding band pass channel. For example, if this relation is less than four, then a low pass filter with a frequency of a quarter of the laser pulse rate can be applied to the rectified band pass signal to extract the envelope component. Alternatively, the upper frequency limit can be set with reference to the phase locking limit for normal hearing, i.e., 1000 pps. FIG. 9 shows constant-rate optical stimulation pulses at 8000 pps amplitude modulated with the envelope component of the band pass signal on the rising positive slope of the envelope component. In FIG. 9, the fast oscillating line shows the band pass signal of the syllable "bet" with frequency boundaries of 3500 and 4700 Hz, the pure positive line is the envelope component signal, the slow varying line around zero amplitude is the first derivative (slope) of the envelope component signal, and the vertical black bars are the optical stimulation pulses. The generation of optical stimulation pulses may be based on the fine structure component for low frequency bands as described before and based on the envelope component for higher frequency bands.

Embodiments of the invention may be implemented in part any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for generating optical stimulation signals to optical stimulation contacts in an implanted cochlear implant array, the method comprising:
    transforming an input sound signal into a plurality of band pass signals each representing an associated band of audio frequencies, wherein each band pass signal comprises a plurality of signal components including:
        i. an envelope component characterizing loudness of the band pass signal, and
        ii. a fine structure component characterizing temporal details of the band pass signal;
    half wave rectifying one or more of the signal components of each band pass signal to remove negative phase signals;
    determining signal slope corresponding to rate of change of the rectified one or more signal components;
    generating a plurality of constant-rate optical stimulation pulses for one or more given band signals only when the rectified one or more signal components has a positive signal slope; and
    amplitude modulating the optical stimulation pulses based on the corresponding fine structure or envelope component to develop the optical stimulation signals for delivery by the optical stimulation contacts to adjacent auditory neural tissue.

2. The method according to claim 1, wherein amplitude modulating the optical stimulation pulses is further based on patient-specific stimulation characteristics.

3. The method according to claim 1, wherein for a given band pass signal the fine structure component is half wave rectified.

4. The method according to claim 1, wherein for a given band pass signal the envelope component is half wave rectified.

5. The method according to claim 1, wherein generating the plurality of constant-rate optical stimulation pulses commences at positive slopes of the rectified one or more signal components.

6. A system for generating optical stimulation signals to optical stimulation contacts in an implantable cochlear implant array, the system comprising:
    a signal filter bank that transforms an input sound signal into a plurality of band pass signals each representing an associated band of audio frequencies, wherein each band pass signal comprises a plurality of signal components including:
        i. an envelope component characterizing loudness of the band pass signal, and
        ii. a fine structure component characterizing temporal details of the band pass signal;
    a signal processing module that processes the band pass signals including:
        i. half wave rectifying one or more of the signal components of each band pass signal to remove negative phase signals,
        ii. determining signal slope corresponding to rate of change of the rectified one or more signal components, and
        iii. generating a plurality of constant-rate optical stimulation pulses for one or more given band signals only when the rectified one or more signal components has a positive signal slope; and
    a pulse mapping and shaping module that amplitude modulates the optical stimulation pulses based on the corresponding fine structure or envelope component to develop the optical stimulation signals for delivery by the optical stimulation contacts to adjacent auditory neural tissue.

7. The system according to claim 6, wherein the pulse mapping and shaping module amplitude modulates the optical stimulation pulses based on the corresponding envelope component and on patient-specific stimulation characteristics.

8. The system according to claim 6, wherein for a given band pass signal the signal processing module half wave rectifies the fine structure component.

9. The system according to claim 6, wherein for a given band pass signal the signal processing module calculates the slope of the envelope component.

10. The system according to claim 6, wherein the signal processing module commences generating the plurality of constant-rate optical stimulation pulses at positive slopes of the rectified one or more signal components.

11. A non-transitory tangible computer-readable medium having instructions thereon for generating optical stimulation signals to optical stimulation contacts in an implantable cochlear implant array, the instructions comprising:
    transforming an input sound signal into a plurality of band pass signals each representing an associated band of audio frequencies, wherein each band pass signal comprises a plurality of signal components including:
        i. an envelope component characterizing loudness of the band pass signal, and
        ii. a fine structure component characterizing temporal details of the band pass signal;
    half wave rectifying one or more of the signal components of each band pass signal to remove negative phase signals;
    determining signal slope corresponding to rate of change of the rectified one or more signal components;
    generating a plurality of constant-rate optical stimulation pulses for one or more given band signals only when the rectified one or more signal components has a positive signal slope; and amplitude modulating the optical stimulation pulses based on the corresponding fine structure or envelope component to develop the optical stimulation signals for delivery by the optical stimulation contacts to adjacent auditory neural tissue.

12. The non-transitory tangible computer-readable medium according to claim 11, wherein amplitude modulating the optical stimulation pulses is further based on patient-specific stimulation characteristics.

13. The non-transitory tangible computer-readable medium according to claim 11, wherein for a given band pass signal the fine structure component is half wave rectified.

14. The non-transitory tangible computer-readable medium according to claim 11, wherein for a given band pass signal the slope of the envelope component is computed.

15. The non-transitory tangible computer-readable medium according to claim 11, wherein generating the plurality of constant-rate optical stimulation pulses commences at positive slopes of the rectified one or more signal components.

\* \* \* \* \*